United States Patent [19]

Nüsslein et al.

[11] 4,251,260
[45] Feb. 17, 1981

[54] 2-(DIMETHYLCARBAMOYLIMINO)-BENZ-THIAZOLINE-3-ID-SALTS, USED IN SELECTIVE WEED CONTROL

[75] Inventors: Ludwig Nüsslein; Friedrich Arndt, both of Berlin, Fed. Rep. of Germany

[73] Assignee: Schering AG, Berlin and Bergkamen, Fed. Rep. of Germany

[21] Appl. No.: 928,883

[22] Filed: Jul. 28, 1978

Related U.S. Application Data

[63] Continuation of Ser. No. 799,324, May 23, 1977, abandoned.

[30] Foreign Application Priority Data

May 31, 1976 [DE] Fed. Rep. of Germany ....... 2624823

[51] Int. Cl.³ .............................................. A01N 43/78
[52] U.S. Cl. ........................................ 71/90; 548/163
[58] Field of Search ............................ 71/90; 260/305

[56] References Cited

U.S. PATENT DOCUMENTS

| | | | |
|---|---|---|---|
| 2,756,135 | 7/1956 | Searle | 71/90 |
| 3,565,901 | 2/1971 | Cebalo | 71/90 X |

Primary Examiner—Catherine L. Mills
Attorney, Agent, or Firm—Michael J. Striker

[57] ABSTRACT 2-(dimethylcarbamoylimino)-benzthiazoline-3-id-salts of the formula

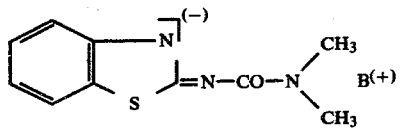

in which $B^{(+)}$ is a univalent metal equivalent. The compounds have herbicidal activity and may be used in herbicidal compositions.

4 Claims, No Drawings

2-(DIMETHYLCARBAMOYLIMINO)-BENZ-THIAZOLINE-3-ID-SALTS, USED IN SELECTIVE WEED CONTROL

This is a continuation of application Ser. No. 799,324, filed May 23, 1977, now abandoned.

BACKGROUND OF THE INVENTION

The invention relates to new 2-(dimethylcarbamoylimino)-benzthiazoline-3-id-salts.

1-(benzthiazol-2-yl)-urea-derivatives are known as herbicidally active compounds (U.S. Pat. No. 2,756,135). However, their activity is not adequate in all cases.

It is therefore an object of the present invention to provide for herbicidal compounds which have a superior action against weeds and at the same time a broad spectrum of selectivity in regard to agricultural plants.

SUMMARY OF THE INVENTION

This object is solved by a compound or a composition containing a compound as active ingredient of the formula

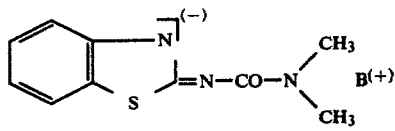

in which $B^{(+)}$ is univalent metal equivalent.

The compounds of the invention are characterized by a broad herbicidal activity when applied either to the ground or to the leaves of the plants. They can be used for monocotyl or dicotyl weeds.

They are of particular use for grassy and other weeds of the genera Stellaria, Senecio, Matricaria, Lamium, Centaurea, Amaranthus, Chrysanthemum, Ipomea, Polygonum, Alopecurus, Digitaria, Poa, and others.

The amounts to be used are between about 1 and 5 kg of active agent per about 2.5 acres.

A particularly high selectivity is possessed by the compounds in regard to peanuts, potatoes, peas, maize, rice, seed-sorghum, wheat and barley.

DETAILS OF THE INVENTION AND PREFERRED EMBODIMENTS

The compounds of the invention can either be used alone or intermixed with each other or in mixture with other active agents. Depending on the purpose, for instance, the following herbicidal agents may be mixed with the compounds of the invention and, if desired, such mixture may be effected only immediately prior to application:
substituted anilines,
substituted aryloxycarboxylic acids and their salts, esters and amides,
substituted ethers,
substituted arsonic acids and their salts, esters and amides,
substituted benzimidazoles,
substituted benzisothiazoles,
substituted benzthiadiazinone dioxides,
substituted benzoxazines,
substituted benzoxazinones,
substituted benzthiazoles,
substituted benzthiadiazoles,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkyl-thio- or dithiophosphates
substituted quinazolines,
substituted cycloalkylamidocarbonylthiol acids and their salts, esters and amides,
substituted cycloalkylcarbonylamido-thiazoles,
substituted dicarboxylic acids and their salts, esters and amides,
substituted dihydrobenzofuranylsulfonates,
substituted disulfides,
substituted dipyridylium salts,
substituted dithiocarbamates,
substituted dithiophosphoric acids and their salts, esters and amides,
substituted urea derivatives,
substituted hexahydro-1H-carbothioates,
substituted hydantoines,
substituted hydrazides,
substituted hydrazonium salts,
substituted isoxazolpyrimidones,
substituted imidazoles,
substituted isothiazolpyrimidones,
substituted ketones,
substituted naphthoquinones,
substituted aliphatic nitriles,
substituted aromatic nitriles,
substituted oxadiazoles,
substituted oxadiazinons,
substituted oxadiazolidindiones,
substituted oxadiazinediones,
substituted phenols and their salts and esters,
substituted phosphonic acids and their salts, esters and amides,
substituted phosphoniumchlorides,
substituted phosphonalkylglycines,
substituted phosphites,
substituted phosphoric acids and their salts, ester and amides,
substituted piperidines,
substituted pyrazoles,
substituted pyrazolalkylcarboxylic acids and their salts, esters, and amides,
substituted pyrazolium salts,
substituted pyrazoliumalkylsulfates,
substituted pyridazines,
substituted pyrimidines,
substituted pyrrolidones,
substituted pyridazones,
substituted pyridine-carbonic acids and their salts, esters and amides,
substituted pyridines,
substituted pyridinecarboxylates,
substituted pyridinone,
substituted pyrimidone,
substituted pyrrolidine-carboxylic acids and their salts, esters and amides,
substituted pyrrolidines,
substituted arylsulfonic acids and their salts, esters and amides,
substituted styrenes,
substituted tetrahydro-oxadiazindiones, substituted tetrahydromethanoindenes,
substituted tetrahydro-diazol-thiones,
substituted tetrahydro-thiadiazine-thiones,
substituted tetrahydro-thiadiazolediones,
substituted thiadiazoles,
substituted aromatic thiocarboxylic acid amides,
substituted thiocarboxylic acids and their salts, esters and amides,
substituted thiolcarbamates,
substituted thiophosphoric acids and their salts, esters and amides,
substituted triazines,
substituted triazoles
substituted tetrahydro-oxadiazoldiones,
substituted thiourea derivatives,
substituted uracils, and
substituted urethidindiones.

It is also possible to use other additives, for instance, non-phytotoxic agents which in herbicides result in a synergistic increase of activity as for instance wetting agents, emulsifying agents, solvents and oily additives.

The compounds of the invention and their mixture are preferably used in the form of overall compositions such as powders, dusting agents, granulates, solutions, emulsions or suspensions. The compositions should include a liquid and/or solid carrier material or diluents and, if desired, wetting, adhesion promoting, emulsifying and/or dispersion agents.

Suitable liquid carrier materials are, for instance, water, aliphatic and aromatic hydrocarbons, such as benzene, toluene, xylene, cyclohexanone, isophorone, dimethylsulfoxide, dimethylformamide, and furthermore mineral oil fractions.

Solid carrier materials are, mineral earths, for instance tonsil, silica gel, talcum, kaolin, attaclay, limestone, silicic acid and plant products, for instance flours.

There may also be added surface active agents, such as, for instance calciumlignosulfonate, polyoxyethylenealkylphenylether, naphthalene-sulfonic acids and their salts, phenolsulfonic acid and their salts, formaldehyde condensation products, fatty alcoholsulfates as well as substituted benzosulfonic acids and their salts.

The amount of the active agent or agents in the compositions can be varied widely. For instance, the compositions may contain between about 10 and 80% by weight of active agents, about 90 to 20% by weight of liquid or solid carrier materials and, if desired, up to 20% by weight of surface active agents.

The application of the compounds can be effected in conventional manner, for instance, by using water as the carrier liquid in spray amounts of about 100 to 1000 liter to about 2.5 acres.

An application of the compounds is possible both in the so-called "low-volume" and "ultra-low-volume" process as also in the form of so-called microgranulates.

Among the compounds of the invention those are preferred in which $B^{(+)}$ in the above formula I is an alkali metal cation and particularly is a lithium, sodium or potassium cation.

The compounds of the invention are salts which are present in ionic form according to the following polarity border cases

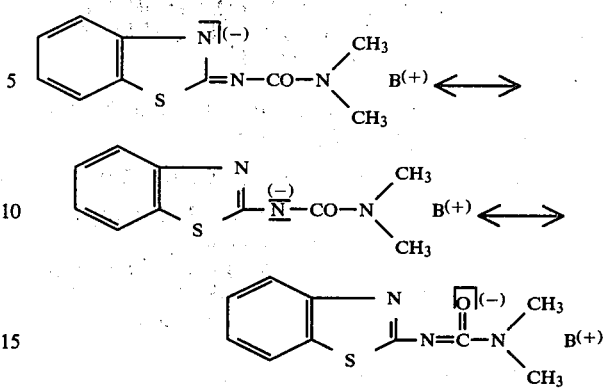

A more general formulation would be as follows:

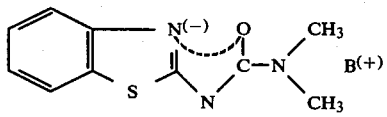

To simplify the expression, not all of the just-given border cases were considered in the above formula I.

The compounds of formula I are novel compounds which may be made in several ways.

I. 2-(dimethylcarbamoylimino)-benzthiazoline-3-carboxylic acid derivatives of the formula

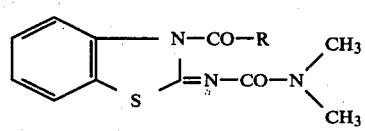

II are reacted with metal compounds of the formula

III so as to open up the compound of formula II. The reaction may take place upon use of a solvent.

II. Another way of making the compounds of the invention would be reacting 1-(benzthiazol-2-yl)-3,3-dimethylurea derivative of the formula

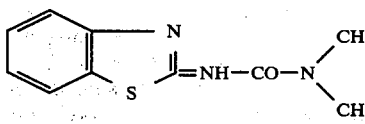

IV with a metal compound of the formula

III

Again the reaction may be effected in a solvent.

$B^{(+)}$ in these formulas has the same meaning as in formula I, while $Y^{(-)}$ is a hydride-, hydroxide-, lower alcoholate- of 1 to 4 carbon atoms or amide anion and R is alkoxy of 1 to 6 carbon atoms or is dimethylamino.

The reaction between the components may be effected at temperatures between about 0° and 120° C. and preferably at room temperature. For the synthesis the components are preferably used in about equimolar amounts.

As reaction media there may be used polar organic solvents, either as such or in admixture with water. Their selection by generally established principles depends on the type of the metal compounds $B^{(+)}Y^{(-)}$.

As solvents or suspension agents there may be named the following: acid amides like dimethylformamide, acid nitriles such as acetonitrile, alcohols, such as methanol, ethanol or isopropanol, ethers, as for instance tetrahydrofuran or dioxane and many others.

Regarding the isolation of the compounds of the invention this may be effected if they are of low solubility by filtration. If they are of a better solubility they may be obtained by distilling off the solvents used which can be done at normal or reduced pressure, or the isolation may be effected by precipitation with less polar organic solvents, for instance, ketones or ethers such as diisopropylether and others.

The following examples will further illustrate the making of the compounds of the invention:

EXAMPLE 1

1.15 g of 2-(dimethylcarbamoylimino)-benzthiazoline-3-carboxylic acid methylester of a melting point of 134° C. were dissolved upon heating at 70° C. in 30 ml ethanol and were then reacted while being stirred with 0.27 g 85% potassium hydroxide dissolved in 10 ml ethanol. During the dropwise addition of the potassium hydroxide the potassium salt is already being precipitated.

The reaction mixture is then still stirred for 15 minutes whereupon the reaction vessel is cooled with ice water and the precipitated potassium salt is then removed by suction and dried in a vacuum at 120° C. There are thus obtained 0.90 g (84.6% of the theoretical value) of 2-dimethylcarbamoylimino)-benzthiazoline-3id, potassium salt.

Melting point: 298° C. (upon decomposition).
Empirical formula: $C_{10}H_{10}KN_3OS$; mol.wt. 259.38
Analysis: theoretical: C 46.31% H 3.89% N 16.20% K 15.07%. obtained: C 46.36% H 4.13% N 16.04% K 15.60%.

EXAMPLE 2

2 g of sodium hydroxide dissolved in 100 ml methanol were added dropwise to a suspension of 11.05 g of 1-(benzthiazol-2-yl)-3,3-dimethylurea in 150 ml methanol while stirring the mass. There was thus formed a clear solution from which the methanol was distilled off in a vacuum. The residual mass was washed with acetonitrile and dried in a vacuum.

The yield was 11.0 g (90.6% of the theoretical value) of 2-(dimethylcarbamoylimino)-benzthiazoline-3-id, sodium salt of the melting point 319°–321° C.

Empirical formula: $C_{10}H_{10}N_3NaOS$; mol.wt. 243.27.

Analysis: theoretical: C 49.37% H 4.14% N 17.27% Na 9.45%. obtained: C 49.16% H 4.42% N 17.10% Na 9.62%.

In analogous manner the corresponding lithium salt of 2-(dimethylcarbamoylimino)-benzthiazoline-3-id having a melting point of 288° C. (decomposition) was made.

The compounds of the invention are colorless, non-smelling crystalline substances among which the potassium salt has a good solubility in diethylene glycol.

The sodium derivative in addition is soluble in water and polar organic solvents such as carboxylic acid amides, for instance dimethylformamide, sulfoxides, for instance dimethylsulfoxide, and lower alcohols, for instance methanol and ethanol.

The lithium compound in addition is soluble in carboxylic acid nitriles, such as for instance acetonitrile.

The following examples will illustrate the activity and use of the compounds of the invention.

EXAMPLE 3

The compounds listed in the following Table 1 were applied in a hot house in amounts of 5 kg of active agent per about 2.5 acres dissolved in 600 liters of water per about 2.5 acres. The application was effected to Sinapis and Solanum as test compounds in pre- and postemergent use.

Three weeks after the treatment the results were evaluated on the following scale from
 0=no effect at all to
 4=destruction of the plants.

As appears from Table I a destruction of the test plants was obtained in all cases:

TABLE I

| Compound of the Invention | Preemergence application | | Postemergence application | |
|---|---|---|---|---|
| | Sinapis | Solanum | Sinapis | Solanum |
| 2-(dimethylcarbamoylimino)-benzthiazoline-3-id, sodium salt | 4 | 4 | 4 | 4 |
| 2-(dimethylcarbamoylimino)-benzthiazoline-3-id, lithium salt | 4 | 4 | 4 | 4 |
| 2-(dimethylcarbamoylimino)-benzthiazoline-3-id, potassium salt | 4 | 4 | 4 | 4 |

EXAMPLE 4

The plants listed in the following Table II were treated in a hot house in a preemergence application with the indicated compounds in amounts of 1 kg of active agent per about 2.5 acres. The compounds were employed for this purpose as aqueous solutions or suspensions in 500 liters of water per about 2.5 acres and were applied in uniform manner to the ground.

The results show that the compounds of the invention contrary to the comparison compound have a high degree of selectivity.

TABLE II

| Preemergence application Compounds of the Invention | peanuts | potatoes | peas | maize | rice | seed-sorghum | Stellaria m. | Senecio v. | Matricaria ch. |
|---|---|---|---|---|---|---|---|---|---|
| 2-(dimethylcarbamoylimino)-benzthiazoline-3-id, sodium salt | 10 | 10 | 10 | 8 | 8 | — | 0 | 0 | 0 |
| 2-(dimethylcarbamoylimino)-benzthiazoline-3-id, lithium-salt | 10 | 10 | 8 | 8 | 10 | 8 | 0 | 0 | 0 |

TABLE II-continued

| Comparison compound | | | | | | | | | |
|---|---|---|---|---|---|---|---|---|---|
| 1-(benzthiazol-2-yl)-3,3-dimethylurea | 8 | 9 | 2 | 9 | 8 | 4 | 0 | 0 | 0 |
| untreated | 10 | 10 | 10 | 10 | 10 | 10 | 10 | 10 | 10 |

| Preemergence application Compounds of the Invention | Lamium a. | Cen- taurea c. | Amaran- thus r. | Chrysan- themum s. | Ipomea p. | Poly- gonum l. | Alope- curus m. | Digi- taria s. | Poa a. |
|---|---|---|---|---|---|---|---|---|---|
| 2-(dimethylcarbamoylimino)-benzthiazoline-3-id, sodium salt | 0 | 0 | 0 | 0 | 0 | 0 | 0 | 0 | 0 |
| 2-(dimethylcarbamoylimino)-benzthiazoline-3-id, lithium-salt | 0 | 0 | 0 | 0 | 0 | 0 | 0 | 0 | 0 |
| Comparison compound | | | | | | | | | |
| 1-(benzthiazol-2-yl)-3,3-dimethylurea | 0 | 0 | 0 | 0 | 0 | 0 | 0 | 0 | 0 |
| untreated | 10 | 10 | 10 | 10 | 10 | 10 | 10 | 10 | 10 |

Scale
0 = destruction of the plant
10 = no injury to the plant

EXAMPLE 5

The plants listed in the following Table III were treated in a hot house in a postemergence application with the listed compounds in amounts of 1 kg of active agent per about 2.5 acres. The compounds in this case were used as aqueous solutions or suspensions in 500 liters of water for about 2.5 acres and were sprayed in a uniform manner onto the plants.

Three weeks after treatment it was again found that the compounds of the invention showed a high selectivity together with an excellent action against the weeds. The comparison compound did not have this degree of selectivity.

The area of ground referred to in the above discussion and tests was originally determined as 1 hectare which for simplicity was converted to correspond to about 2.5 acres in the Anglo-Saxon system.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of controlling weed growth in cereal crops, comprising treating said crops with a composition comprising between about 10 and 80 weight-% of a compound of the formula

TABLE III

| Compounds of the Invention | bush beans | pea- nuts | potatoes | maize | wheat | barley | rice | seed- sorghum | Stel- laria m. | Sene- cio v. | Matri- caria ch. | Lami- um a. |
|---|---|---|---|---|---|---|---|---|---|---|---|---|
| 2-(dimethylcarbamoylimino)-benzthiazoline-3-id, sodium salt | 8 | 10 | 10 | 10 | 8 | 8 | 10 | 10 | 0 | 0 | 0 | 0 |
| 2-(dimethylcarbamoylimino)-benzthiazoline-3-id, lithium salt | — | 10 | 10 | 10 | 10 | 10 | 10 | 10 | 0 | 0 | 0 | 0 |
| 2-(dimethylcarbamoylimino)-benzthiazoline-3-id, potassium salt | 10 | 10 | 8 | 9 | 10 | 10 | 10 | 10 | 0 | 0 | 0 | 0 |
| Comparison compound | | | | | | | | | | | | |
| 1-(benzthiazole-2-yl)-3,3-dimethyl urea | 1 | 5 | 1 | 5 | 4 | 5 | — | — | 0 | 0 | 0 | 0 |
| untreated | 10 | 10 | 10 | 10 | 10 | 10 | 10 | 10 | 10 | 10 | 10 | 10 |

| Compounds of the Invention | Cen- taurea c. | Amaran- thus r. | Gal- ium a. | Chrysan- themum s. | Ipo- mea p. | Poly- gonum l. | Alope- curus m. | Echni- noch- loa c.g. | Se- taria i. | Digi- taria s. | Poa a. |
|---|---|---|---|---|---|---|---|---|---|---|---|
| 2-(dimethylcarbamoylimino)-benzthiazoline-3-id, sodium salt | 0 | 0 | 0 | 0 | 0 | 0 | 0 | 0 | 0 | 0 | 0 |
| 2-(dimethylcarbamoylimino)-benzthiazoline-3-id, lithium salt | 0 | 0 | 0 | 0 | 0 | 0 | 0 | 0 | 0 | 0 | 0 |
| 2-(dimethylcarbamoylimino)-benzthiazoline-3-id, potassium salt | 0 | 0 | 0 | 0 | 0 | 0 | 0 | 0 | 0 | 0 | 0 |
| Comparison compound | | | | | | | | | | | |
| 1-(benzthiamole-2-yl)-3,3-dimethyl urea | 0 | 0 | 0 | 0 | 0 | 0 | 0 | 0 | 0 | 0 | 0 |
| untreated | 10 | 10 | 10 | 10 | 10 | 10 | 10 | 10 | 10 | 10 | 10 |

Scale
0 = destruction of the plant
10 = no injury to the plant

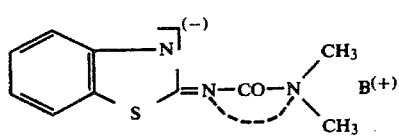
wherein $B^{(+)}$ is an alkali metal cation as active agent, and about 90 to 20 weight-% carrier material at a rate of between about 1 and 5 kg active agent/ha.
2. A method as defined in claim 1, wherein $B^{(+)}$ is a lithium cation.
3. A method as defined in claim 1, wherein $B^{(+)}$ is a sodium cation.
4. A method as defined in claim 1, wherein $B^{(+)}$ is a potassium cation.
* * * * *